(12) United States Patent
Sayer et al.

(10) Patent No.: US 7,617,054 B2
(45) Date of Patent: Nov. 10, 2009

(54) METHOD AND APPARATUS FOR ANALYSING NUCLEIC ACID SEQUENCE

(75) Inventors: David Charles Sayer, East Fremantle (AU); Damian Mark Goodridge, Darlington (AU)

(73) Assignee: Conexio 4 PTY Ltd, East Fremantle, WA (AU)

( * ) Notice: Subject to any disclaimer, the term of this patent is extended or adjusted under 35 U.S.C. 154(b) by 537 days.

(21) Appl. No.: 11/185,429

(22) Filed: Jul. 20, 2005

(65) Prior Publication Data

US 2006/0035253 A1    Feb. 16, 2006

Related U.S. Application Data

(60) Provisional application No. 60/590,059, filed on Jul. 21, 2004.

(30) Foreign Application Priority Data

Jul. 20, 2004    (AU) .............................. 2004903981

(51) Int. Cl.
*G06F 19/00* (2006.01)
*C12Q 1/68* (2006.01)
(52) U.S. Cl. ............................................. 702/19; 435/6
(58) Field of Classification Search .................. None
See application file for complete search history.

(56) References Cited

U.S. PATENT DOCUMENTS

| 5,365,455 A | 11/1994 | Tibbetts et al. |
| 6,300,063 B1 | 10/2001 | Lipshutz et al. |
| 2003/0211504 A1 | 11/2003 | Fechtel et al. |
| 2004/0215401 A1 | 10/2004 | Krane et al. |

FOREIGN PATENT DOCUMENTS

| EP | 1092782 A2 | 4/2001 |
| WO | 9914369 A1 | 3/1999 |
| WO | 0161028 A2 | 8/2001 |
| WO | 03102211 A2 | 12/2003 |
| WO | 2004015609 A2 | 2/2004 |

OTHER PUBLICATIONS

Nickerson et al. PolyPhred: automating the detection and genotyping of single nucleotide substitutions using fluorescence-based resequencing Nucleic Acids Research vol. 25, pp. 2745-2751 (1997).*

Ewing et al. Base-calling of Automated Sequencer Traces Using Phred. I. Accuracy Assessment Genome Research vol. 8, pp. 175-185 (1998).*

International Search Report dated Aug. 31, 2005 issued in PCT/AU2005/001065.

* cited by examiner

*Primary Examiner*—John S Brusca
(74) *Attorney, Agent, or Firm*—Lando & Anastasi, LLP

(57) ABSTRACT

A method of analyzing nucleic acid sequence data produced by automated sequencer comprises scaling the data according to a map of relative heights of homozygous base data. An apparatus for conducting the method comprises means for scaling the data according to a map of relative heights of homozygous base data.

40 Claims, 13 Drawing Sheets

For each trace with a peak count of greater than zero, divide the average height by the peak count.

METHOD AND APPARATUS FOR ANALYSING NUCLEIC ACID SEQUENCE

CROSS REFERENCE TO RELATED APPLICATIONS

This application claims priority under 35 U.S.C. § 119(e) to U.S. Provisional Application Ser. No. 60/590,059, entitled "METHOD FOR ANALYSING NUCLEIC ACID SEQUENCE," filed on Jul. 21, 2004, which is herein incorporated by reference in its entirety.

Foreign priority benefits are claimed under 35 U.S.C. §119 (a)-(d) of Australian application number 2004903981, filed Jul. 20, 2004, which is hereby incorporated by reference in its entirety.

Computer Program Listing Appendix

A Computer Program Listing Appendix stored on compact disc, submitted herewith in duplicate, is provided and hereby incorporated by reference in its entirety in this application. A total of two (2) discs are submitted. The second disc is a duplicate of the first disc. Each disc contains the following files: Appendix A.txt, size 16 KB, created on Aug. 25, 2009; and Appendix B.txt, size 9 KB, created on Aug. 25, 2009.

FIELD OF INVENTION

The present invention relates generally to the investigation of the sequencing of nucleic acid, particularly DNA. More particularly, the present invention relates to a method of and apparatus for analyzing a sequence generated by an automated DNA sequencer.

BACKGROUND

Nucleic acid sequencing and in particular DNA sequencing is essential to the practice of biotechnology, genetic engineering and many other disciplines that rely on the need to determine the genetic information contained in DNA. The sequencing of DNA (herein termed "DNAS") is the process of determining the sequence of nucleotides that comprise a strand of DNA or can be used to identify the type of nucleotide at one or more specific positions. A nucleotide usually consists of a pentose sugar, a phosphate and 1 of 4 possible nitrogenous bases, denoted A for adenine, G for guanine, C for cytosine, and T for thymine. The sequence of these bases uniquely describes each piece of DNA. DNAS is a crucial step in genetic engineering and biotechnology, since it provides the precise code of genetic information contained in a sample of DNA.

DNA is typically double stranded and hence, the term base pairs is often used, since each base of one strand is opposed by its complimentary base on the other strand. There are an enormous number of bases that need to be sequenced in order to read a piece of DNA. Even a simple piece of DNA from a bacteria cell would likely comprise several thousand bases.

DNA sequencing is traditionally a very labor intensive process. Much has been written about DNA sequencing and genetic engineering and the reader is referred to the many references on this subject, which will provide additional background information.

Two methods of DNA sequencing have been developed. The first is by Maxam and Gilbert (1977) and is described in Proc. Natl. Acad. Sci. USA, Vol. 74, page 560. The second method is described in Proc. Natl. Acad. Sci. USA, by Sanger et al., (1977), Vol. 74, page 5463. The Sanger method involves the generation of DNA fragments by the enzymatic extension of a small piece of DNA called a primer. The primer is extended following the addition of the appropriate bases by an enzyme called polymerase. The sequencing reaction includes bases that permit DNA extension (CEB) and bases that have been chemically modified to terminate DNA extension (CTB). Termination of DNA extension results in the generation of a DNA fragment. The sequencing reaction contains many copies of DNA and is a dynamic system of DNA extension and DNA termination, where at the same site on any strand of DNA a CEB or a CTB is added. This results in the generation of large numbers of pools of fragments where each pool differs in length by a single base.

Once the generation of fragments has been completed the resultant mixture of DNA fragments need to be separated and analyzed. The task of separating the fragments by size to determine what order they are in can be performed by a number of well known techniques. The first methods of manual DNA sequencing utilized polyacrylamide gel electrophoresis techniques to separate the fragments. Polyacrylamide gels have the ability to resolve fragments with a resolution of one base pair, and that resolution is necessary for sequencing. Each fragment is labeled with a radioactive element that typically gives off a beta particle, such as radioactive phosphorus ($^{32}P$). Each of the four samples are then separated in size in their own lane in the gel. The four lanes are typically side by side. After electrophoresis, a piece of x-ray film is placed next to the gel for a number of hours, often a couple of days, to expose the film with the radioactive emissions from the $^{32}P$. When developed, the fragments show up as dark bands on the film and the sequence can then be read from the order in which the bands appeared, from the bottom to the top of the film.

Automating DNAS involves automating the process of detecting the fragments on the electrophoresis medium (e.g. a gel) and then automatically determining the DNA base sequence from the sequence of detected fragments using the above algorithm implemented in a microprocessor. Because of the time needed to expose the x-ray film to the β radiation of the $^{32}P$, and other considerations involving the use of radioisotopes, new methods of tagging and sequencing based on fluorescence were developed. See, for example, Biophysical and Biochemical Aspects of Fluoresene Spectroscopy, edited by T. Gregory Dewey, Plenum Press, 1997; "Large Scale and Automated Sequence Determination," by T. Hunkspillar et al., (1991), Science, Vol. 254, pages 59-67 and "DNA Sequencing: Present Limitations and Prospects for the Future," Barrell, (1991), FASEB Journal, Vol. 5, page 40-45.

Fluorescence tagging of the fragments involves the attachment of a fluorescent compound, or fluorophore, to each fragment analogously to the attachment of the radioactive label to each fragment. These fluorescence labels were found to not adversely affect the process of gel electrophoreses or sequence.

Fluorescence is an optical method that involves stimulating the fluorescent molecule by shining light on it at an optical wavelength that is optimum for that fluorescent molecule. Fluorescent light is then given off by the molecule at a characteristic wavelength that is typically slightly longer than the stimulation wavelength. By focusing the light at the stimulating wavelength down to a point on the gel and then detecting the presence of any optical radiation at the characteristic wavelength of light from the fluorescent molecule, the presence at that point of fragments of DNA tagged with that fluorescent molecule may be determined.

Two methods of implementing an automated DNA sequencing instrument are known in the art. One, reported by Smith et al., (1986), Nature, Vol 321, pages 674-679, puts a different fluorescent tag on each of the four samples of fragments described above. Thus, the sample of fragments that end in the base A are tagged by one fluorophore; the sample of fragments that end in the base G are tagged by another fluorophore, and so on for the other two samples. Each fluorophore can be distinguished by its own stimulation and emission wavelengths of light.

In the Smith et al. method, all four samples are electrophoresed in the same lane together and the differences in their tags are used to distinguish them. That has the advantage that four separate lanes are not used, since the progression of fragments in different lanes is often not consistent with one another and difficulties often arise in determining the sequence as a result.

Another method, reported by Ansor et al., (1986), J. Biochem Biophys. Methods, Vol. 13, pages 315-323 and Nucleic Acids Res., Vol 15(11), pages 4593-4602 (1987), uses one fluorescent tag for all fragments, but employs four separate lanes of gel electrophoresis in a manner that is similar to radioactive labeled sequencing. That approach has the potential disadvantage that four lanes, with different fragment migration rates caused by local temperature variations and other inconsistencies within the gel, could limit the reliability of the sequence determination.

Fluorescence tagging and the detection of natural fluorescence in molecules is a method of analytical chemistry and biology that is well known in the art. The methods described above have been developed for DNA sequencing by the creation of fluorescent tags that can be bound to fragments of DNA. The instruments used to detect fluorescence consist of the following parts. A light source with a broad optical bandwidth, such as a light bulb, or a laser is used as the source of the stimulating light. An optical filter is used to select the light at the desired stimulation wavelength and beam it onto the sample. Optical filters are available at essentially any wavelength and are typically constructed by the deposition of layers of thin film at a fraction of the wavelength of the desired transmission wavelength. The light that exits the optical filter is then applied to the sample to stimulate the fluorescent molecule.

The molecule then emits light at its characteristic fluorescent wavelength. This light is collected by a suitable lens and is then passed through a second optical filter centered at the characteristic wavelength before being brought to a detection device such as a photomultiplier tube, a photoconductive cell, or a semiconductor optical detector. Therefore, only light at the desired characteristic wavelength is detected to determine the presence of the fluorescent molecule.

Whichever automatic DNAS system is used the data generated is analyzed by the computer software of the DNA sequencer to produce a signal, which takes the form of a series of peaks for each of the 4 different colors where each color represents a particular nucleotide base type. The heights of the peaks are rarely uniform and are proportional to the number of fragments in the DNA fragment pool. This is in turn proportional to the amount of DNA that is being sequenced and the rate at which unlabelled nucleotides are incorporated relative to the rate at which labeled nucleotides are incorporated into the extending DNA chain. The scientist or technician has the choice of checking these data to ensure the base calling by the automated sequencer has been performed correctly.

Most DNAS applications involve the identification of sequences of anonymous DNA such as in for example the Human Genome Project. DNAS has also been used to study evolution and population migration by studying sequence diversity of the same region within different individuals of the same or different species. Clinically, DNAS has been used for the detection of mutations in cancer studies and for the detection of viral mutations associated with resistance to anti-viral drugs. One of the most common applications of DNAS is tissue typing, where the genetic matching of tissue types between donors and recipients is critical to the success of transplantation.

For many sequencing based typing applications, DNA from two chromosomes from an individual are sequenced together. At most positions the sequence at the same position on both chromosomes is identical resulting in a single peak (homozygous). However at some positions the sequence is different between the two chromosomes resulting in two peaks at the same position (heterozygous). Each peak is reduced in height compared to when each base is present as homozygous. It is the accurate identification of both bases when they are present at the same position that remains the impediment to widespread use of DNAS for clinical application.

Consequently, there is a need for a method of discriminating between homozygous and heterozygous sequence generated by automatic sequencers. Moreover, there is a need for a method that increases the base calling accuracy for heterozygous sequence and improves the ability to detect low level mutations thereby enabling the quantitation of mutations.

The method of detecting DNA variation in sequence data described in WO/03102211 compares a sequence trace of a reference sequence with the traces of sample sequences, performs an analysis to identify the differences between the two and provides a trace that contains only the difference between the two traces. A disadvantage of this method is that it requires the reference trace sequence and is often inaccurate.

SUMMARY OF INVENTION

Accordingly, in a first aspect, the present invention provides a method for analyzing nucleic acid sequence data produced by automated sequencer comprising scaling the data according to a map of relative heights of homozygous base data.

According to a second aspect of the present invention there is a method of producing a normalized set of electropherogram trace signals of a nucleic acid sequence of a sample comprising:

providing first electropherogram signal data from a first sequence obtained using a given nucleic acid sequencing chemistry, the signal data comprising a trace of the detection signal for each type of base at each base position in the nucleic acid sequence;

creating a relative height map of the intensities of each trace at each base position from the electropherogram signal data;

obtaining second electropherogram signal data of another sample using the same nucleic acid sequencing chemistry;

scaling the data for each base in each trace by the expected height of the base in the relative height map to produce a normalized base data set.

According to a third aspect of the invention there is a method of detecting mixtures of bases in a nucleic acid sequence comprising:

determining whether each base in the scaled data set produced using the above method has a significantly lower height than the expected height and in the event that is does registering the base as a mixture.

Preferably the mixture of bases is a mixture of 2 bases, that is, a heterozygous mixture.

According to a fourth aspect of the invention there is a method of indicating mixtures of bases in a nucleic acid sequence comprising:

displaying the scaled data set produced using the above method, with mixtures of bases being indicated as having a significantly lower height than the expected height of a homozygous base.

According to a fifth aspect of the invention there is a method of sequencing DNA comprising:

providing a sample of tissue;

extracting DNA from the sample of tissue;

amplifying the extracted DNA;

conducting a sequencing reaction on the amplified DNA to produce a mixture of DNA fragments labeled with a nucleotide type indicator;

separating the labeled fragments in an electrophoretic DNA analyzer;

measuring the signals from the separated fragments to determine a sequence;

performing a spacing analysis to determine peak positions for fragments as fragment size varies;

performing a fitting procedure to determine peak characteristics;

scaling each peak according to a relative height map of the expected peak heights of each trace at each base position determined from reference data obtained using the same chemistry in the sequencing reaction.

According to a sixth aspect of the invention there is a method of analyzing a nucleic acid sequence comprising:

mapping the relative signal strength of bases to form a relative height map;

comparing a sample to the map to determine whether the signal strength of a sample is close to the signal strength of the map for each nucleotide type at each base position so that if it is approximately equal to the signal strength of one of the nucleotide types then the nucleotide at that base is considered to be that nucleotide type and is homozygous and if it is approximately half of the expected signal strength then it is a mixture of the nucleotide types.

According to a seventh aspect of the invention there is a method of mapping the relative signal strength of bases to form a relative height map comprising:

a) obtaining a trace signal for each nucleotide type over a plurality of base positions from a sample of DNA;

b) discarding the signal at base positions that are not of sufficiently high quality;

c) discarding the signal at base positions that are not homozygous;

d) mapping the height of the trace signal for each trace for each base position;

e) repeating steps (a), (b), (c) and (d) until the height at all of the bases desired to be mapped are mapped.

Preferably the method further comprises interpreting the normalized data to identify the bases present and producing a text sequence.

Preferably the method further comprises producing the map of relative heights of homozygous base data.

Preferably the map is produced by determining an average intensity of the heights of each base position that is homozygous in a trace of each nucleotide type in the sequence data.

Preferably the map is produced by normalizing the sequence data relative to the average intensity.

Preferably the average intensity for each trace is determined by scaling the height of each base position that is homozygous relative to the highest of the heights of each base position for each trace.

Preferably the map is adjusted by a contribution of the height of each base position that is homozygous for each trace from subsequent samples of sequence data.

Preferably subsequent sequence samples are scaled to provide a small contribution of relative base height at each position to the existing relative height at each corresponding position in the relative height map.

Preferably the sequence data comprises a trace for each nucleotide type, with each trace defined by a series of peaks at base positions in which a nucleotide base of the type corresponding to the trace type is present, wherein the map is produced by finding a scaling factor at each base position in the map that normalizes the peak height of homozygous bases.

Preferably the scaling factor for each base position is determined by taking the highest peak in each trace and dividing it by the height of the peak at that base position for each base position in each trace.

Preferably an average intensity of each trace is calculated.

Preferably the scaling factor for each base position is calculated by dividing average intensity of the respective trace by the peak height at that base position.

Preferably the average intensity is calculated by accumulating a measure of the relative height of each peak that has a non-zero contribution and then dividing this by the number of peaks contributing to the accumulation.

Preferably the scaling factor is adjusted by comparing each base peak height in a subsequent sample to each previous peak height and normalizing the average intensity to unity.

Preferably the relative height for each base is updated by multiplying the height of the sequence data at each base position for each nucleotide type by a corresponding scaling factor of the map.

Preferably an updated relative peak height is determined by adding a small percentage of the peak height of each base multiplied by the scaling factor to the current relative peak height.

Preferably a new sample is added to the relative height map by aligning the new sample with the same bases in the relative height map.

According to an eighth aspect of the present invention there is provided a nucleic acid sequencing apparatus configured to perform one or more of the above methods.

According to a ninth aspect of the present invention there is provided a computer program comprising instructions for controlling a data processing device to conduct one or more of the above methods.

According to a tenth aspect of the present invention there is provided a computer readable storage medium comprising the computer program defined above.

According to an eleventh aspect of the present invention there is provided an apparatus for analyzing nucleic acid sequence data produced by automated sequencer comprising means for scaling the data according to a map of relative heights of homozygous base data.

According to an eleventh aspect of the present invention there is provided an apparatus for analyzing nucleic acid sequence data produced by automated sequencer comprising means for scaling the data according to a map of relative heights of homozygous base data.

According to a twelfth aspect of the present invention there is provided an apparatus for producing a normalized set of electropherogram trace signals of a nucleic acid sequence of a sample comprising:

means for providing electropherogram signal data from a panel of homozygous sequences obtained using a given nucleic acid sequencing chemistry, the signal data comprising a trace of the detection signal for each type of base at each base position in the nucleic acid sequence;

means for creating a relative height map of the intensities of each trace at each base position from the panel signal data;

means for obtaining electropherogram signal data of a sample using the same nucleic acid sequencing chemistry;

means for scaling the data for each base in each trace by the expected height of the base in the relative height map to produce a normalized base data set.

According to a thirteenth aspect of the present invention there is provided an apparatus for detecting heterozygous bases in a nucleic acid sequence comprising:

means for determining whether each base in the scaled data set produced using the above apparatus has a significantly lower height than the expected height and in the event that is does registering the base as heterozygous.

According to a fourteenth aspect of the present invention there is provided an apparatus for indicating heterozygous bases in a nucleic acid sequence comprising:

means for displaying the scaled data set produced using the above apparatus, with heterozygous bases being indicated as having a significantly lower height than the expected height of a homozygous base.

According to a fifteenth aspect of the present invention there is provided an apparatus for sequencing DNA comprising:

means for receiving a sample of tissue;
means for extracting DNA from the sample of tissue;
means for amplifying the extracted DNA;
means for conducting a sequencing reaction on the amplified DNA to produce a mixture of DNA fragments labeled with a nucleotide type indicator;
means for separating the labeled fragments;
means for measuring the signals from the separated fragments to determine a sequence;
means for performing a spacing analysis to determine peak positions for fragments as fragment size varies;
means for performing a fitting procedure to determine peak characteristics;
means for scaling each peak according to a relative height map of the relative heights of each trace at each base position determined from a panel comprising data obtained using the same chemistry in the sequencing reaction.

According to a sixteenth aspect of the present invention there is provided an apparatus for analyzing a nucleic acid sequence comprising:

means for mapping the relative signal strength of bases to form a relative height map;

means for comparing a sample to the map to determine whether the signal strength of a sample is close to the signal strength of the map for each nucleotide type at each base position so that if it is close to the signal strength of one of the nucleotide types then the nucleotide at that base is considered to be that nucleotide type and is homozygous and if it is close to half of the signal strength then it is of the nucleotide types and is heterozygous.

According to a seventeenth aspect of the present invention there is provided an apparatus for mapping the relative signal strength of bases to form a relative height map comprising:

a) means for obtaining a trace signal for each nucleotide type over a plurality of base positions from a sample of DNA;

b) means for discarding the signal at base positions that are not of sufficiently high quality;

c) means for discarding the signal at base positions that are not homozygous;

d) means for mapping the height of the trace signal for each trace for each base position;

wherein the means of (a), (b), (c) and (d) are used again until the height at all of the bases desired to be mapped are mapped.

BRIEF DESCRIPTION OF DRAWINGS

The accompanying drawings are not intended to be drawn to scale. For purposes of clarity, not every component may be labeled in every drawing. In the drawings.

DETAILED DESCRIPTION

Figure 1:
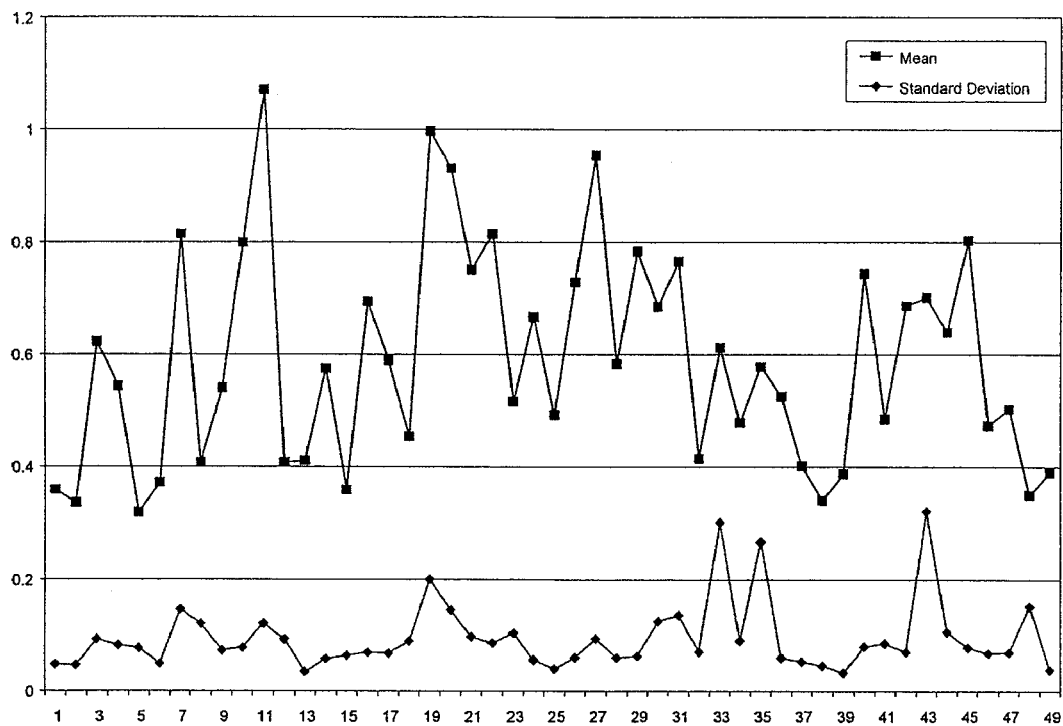
FIG. 1 is a graph of mean peak heights and standard deviations from DNA sequence data using current sequence analysis and base calling algorithms.

This invention is not limited in its application to the details of construction and the arrangement of components set forth in the following description or illustrated in the drawings. The invention is capable of other embodiments and of being practiced or of being carried out in various ways. Also, the phraseology and terminology used herein is for the purpose of description and should not be regarded as limiting.

Before describing the present invention in detail, it is to be understood that this invention is not limited to particularly exemplified methods and may, of course, vary. It is also to be understood that the terminology used herein is for the purpose of describing particular embodiments of the invention only, and is not intended to be limiting which will be limited only by the appended claims.

All publications, patents and patent applications cited herein, whether supra or infra, are hereby incorporated by reference in their entirety. However, publications mentioned herein are cited for the purpose of describing and disclosing the protocols, reagents and vectors which are reported in the publications and which might be used in connection with the invention. Nothing herein is to be construed as an admission that the invention is not entitled to antedate such disclosure by virtue of prior invention.

Furthermore, the practice of the present invention employs, unless otherwise indicated, conventional molecular biological techniques and software engineering within the skill of the art. Such techniques are well known to the skilled worker, and are explained fully in the literature. See, e.g., Sambrook et al., (Molecular Cloning: A Laboratory Manual, 2nd Edition, Cold Spring Harbor Laboratory press (1989); and Bailey, J. E. and Ollis, D. F., Biochemical Engineering Fundamentals, McGraw-Hill Book Company, NY, 1986.

It must be noted that as used herein and in the appended claims, the singular forms "a", "an", and "the" include plural reference unless the context clearly dictates otherwise. Thus, for example, a reference to "a DNA sequence" includes a plurality of such sequences, and a reference to "an isolated DNA molecule" is a reference to one or more molecules, and so forth. Unless defined otherwise, all technical and scientific terms used herein have the same meanings as commonly understood by one of ordinary skill in the art to which this invention belongs. Although any materials and methods similar or equivalent to those described herein can be used to practice or test the present invention, the preferred materials and methods are now described.

This invention relates to a software program capable of sample to sample reproducible determination of the incorporation rate of deoxynucleotides ("CEB"), which permit primer extension and dideoxynucleotides ("CTB"), which terminate primer extension. The invention also relates to apparatus for sequencing nucleic acid and/or a computer configured to analyze data from a sequencing apparatus configured to run the computer software so as to perform the method of the present invention. Such software will run in the memory of a data processing device (CPU) of the computer or sequencing apparatus and may be stored in non-volatile storage means, such as for example a hard disk drive. The non-volatile storage means is loaded with the computer software from a computer readable storage means, such as a compact disk or DVD. Access to the apparatus (or computer) may be provided by a telecommunications network, so that data is provided to the apparatus over the network, which performs the method of the present invention and then outputs the results, possibly again over the network.

Figure 7:
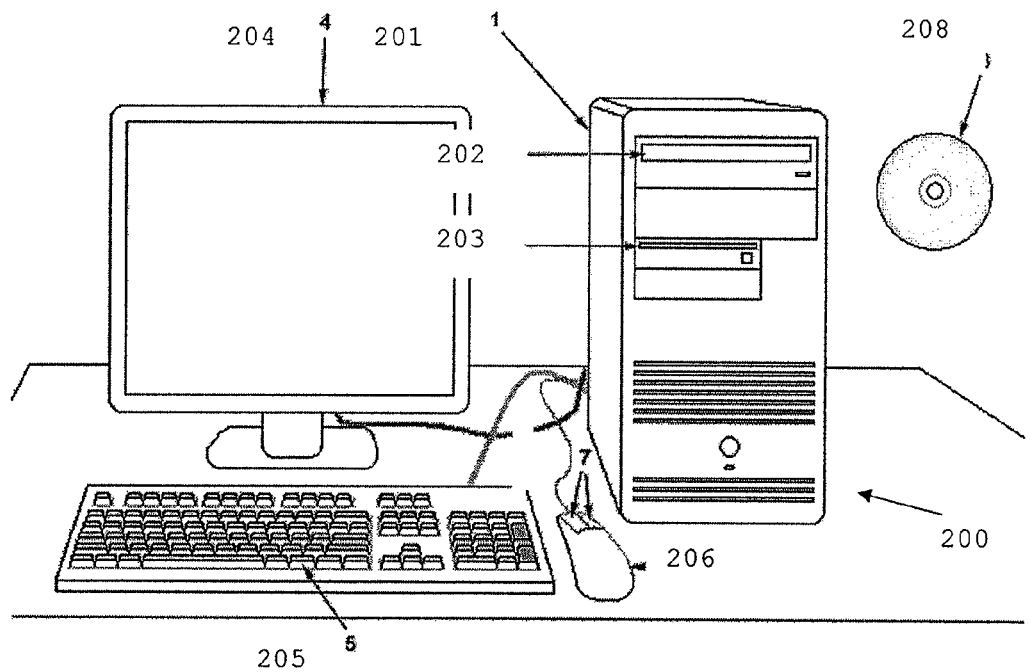
FIG. 7 is a schematic representation of the computer system configured to perform one embodiment of the present invention.

FIG. 7 shows a typical computer system 200 which is configured to perform form embodiments the method of the present invention. The computer system 200 it a typical computer comprising of a case 201, optical drive 202, floppy disk drive 203, monitor 204, keyboard 205, and mouse 206.

A CD-ROM 208 illustrates a computer readable storage media containing a copy of the controlling software which configures and controls the computer system to perform the invention. This software may exist or be distributed on a wide variety of media types including CR-ROM, DVD, Floppy Disk, Fixed Disk, Flash Memory, and others. The case 201 contains a number of components not visible from the outside. An example of this is the fixed hard disk drive 217.

Figure 8:
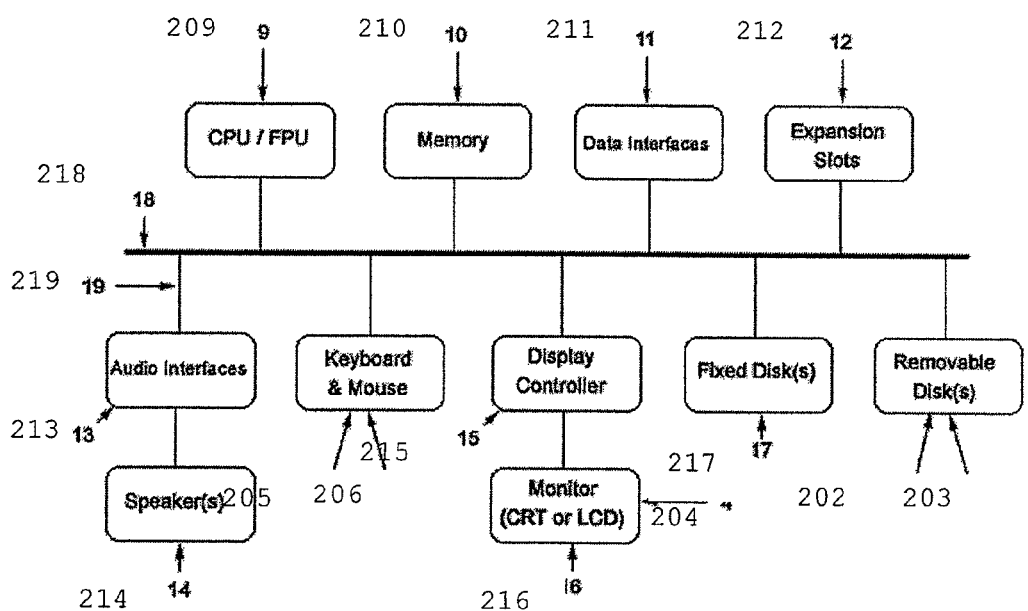
FIG. 8 is a schematic block diagram of components of the computer system of FIG. 7.

FIG. 8 is a block diagram illustrating the relationship between various components of the computer system 200. A bus 218 and connectors 219 represent the complex interconnection between the components of the computer. In reality there are a number of busses and interconnections that a person skilled in the art would be aware of. The diagram is not exhaustive in nature.

System memory 210 is used to contain all or part of the software and intermediate results while executing the software. The Data Interfaces 211 are used to connect the computer system to other devices for input and output. Examples of these are a network interface, a printer port, a USB connection, and a serial interface. Expansion slots 212 exist to allow additional components to be added to the computer system. An Audio Interface 213 and speakers 214 are used to provide audible feedback to the operator. The keyboard 205 and mouse 206 are the primary means of the operator entering information. Note that the mouse could be replaced with a trackball, a touch-screen, a touch pad, a digitizing pad, or other device. The display controller 215 is used to interface to the monitor 204. Fixed disks 217 are usually contained within the case and are used for storage of software and data. Removable disks 202, 203 may be used for transferring software or data. A computer system suitable for use with this invention may have additional subsystems (for example, a barcode scanner, cache memory, or multiple display controllers) or fewer components (it may not have expansion slots or removable disks).

The illustrated computer system 200 is but one that could be used with this invention. Other configurations that would be suitable would be readily apparent to a person with ordinary skills in the art.

Conventional analysis and base calling is performed directly on the "primary" data. (This data in itself is considerably enhanced by the automated DNA sequencer software). The present invention represents the sequence data as a relative factor of how the observed peak deviated from what is expected. This results in peaks of almost the same height at every position where the sequence is the same on both chromosomes (for HLA and other genotyping assays) or at positions that are either totally wildtype or totally mutant (mutation detection assays including HIV drug resistance genotyping). Position within a sequence that contain bases from both chromosomes are easily identified because there will be two peaks, each of which will be significantly reduced in height compared. Base calling is performed on this normalized data resulting in improved accuracy of base calling especially at heterozygous positions or positions that contain a mixture of wildtype and mutant sequences FIG. 1 demonstrates the variable nature of peak heights from sequence data as it is represented using current sequence analysis and base calling algorithms. It shows the variation in peak height at 49 positions within HLAA Exon 2 sequenced in the forward direction over 286 samples. The upper set of values gives the mean relative peak height at each position, while the lower set is the standard deviation.

The present invention increases base call accuracy of all of the sequence and dramatically reduces the requirement for manual checking of DNA sequence electropherograms (sequence editing). Furthermore base calling accuracy is dramatically improved for positions that contain two or more peaks and also improves base calling accuracy at positions containing sequence chemistry, and other, reproducible artifacts. This invention can be applied to the following non-exhaustive list:

1. Sequencing base genotyping of one or more loci simultaneously.
2. Sequencing based genotyping of loci of any organism.
3. Single nucleotide polymorphism detection.
4. Mutation screening.
5. Mutation quantitation.
6. Comparison of frequencies of polymorphisms between different pools of DNA.

During chain extension the polymerase has a "choice" of whether to add CTB or CEB. The rate at which CTB are added relative to CEB varies greatly from site to site. At a site where the rate of addition of CTB is high a greater number of DNA fragments will be produced and the resulting peak height will be high. Similarly if the rate of addition of CTB is low, there will be fewer DNA fragments and low peak heights. The implications of variable incorporation rates when simultaneously sequencing DNA from different origins (i.e. DNA from different chromosomes, or simultaneous sequencing of different viral species, as in the case of HIV sequencing) is that if two bases are sequenced simultaneously at one position and one of the CTB has a reduced incorporation rate the resulting peak may be so low that it is indistinguishable from background or may not be detected. In addition to the variable peaks heights the "dose response" also varies. That is, if two bases are sequenced simultaneously, one from each chromosome, the resulting peak heights will not necessarily be 50% of the homozygous peak height.

The inventors have found that despite the variability in peak heights within a sequence, the rate of incorporation of CTB and CEB at any position is highly reproducible so that if an analogous region of DNA is sequenced from different individuals the relative peak heights will be the same, within a small percentage of variability, at analogous positions within the sequence. This finding is used in a scaling process of the present invention.

The high level of reproducibility is also true for different genes that share similar sequence and is independent of the origin of the DNA. For example, if two or more analogous regions of DNA from diverse organisms, i.e. bacteria and humans, the rate of incorporation of CEB and CTB during DNAS will be sufficiently reproducible as to be considered identical. Thus the relative peak heights will be considered identical.

Figure 2A:
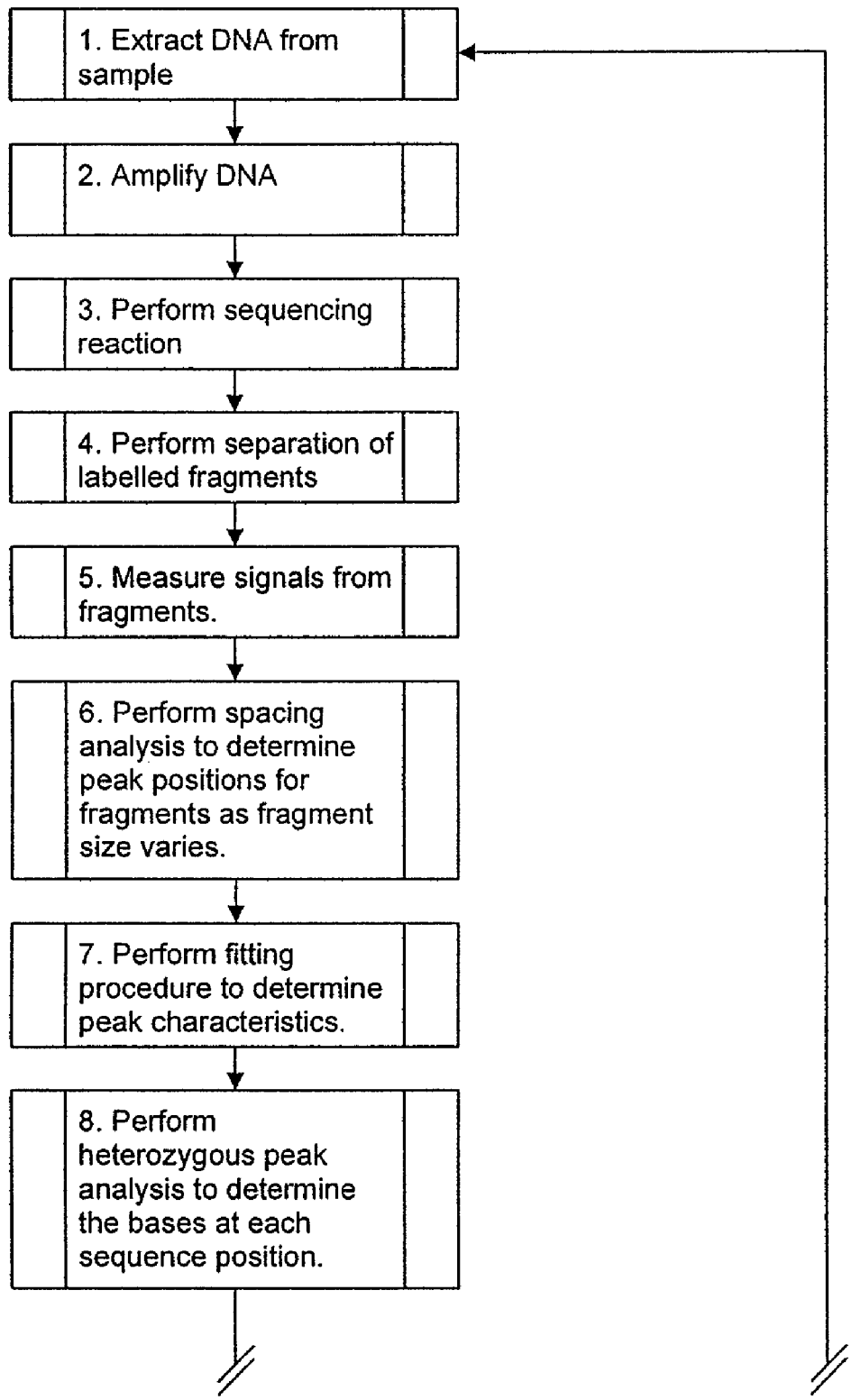
FIGS. 2A-2B illustrate a flow chart showing first preferred form of the present invention.
Figure 2B:
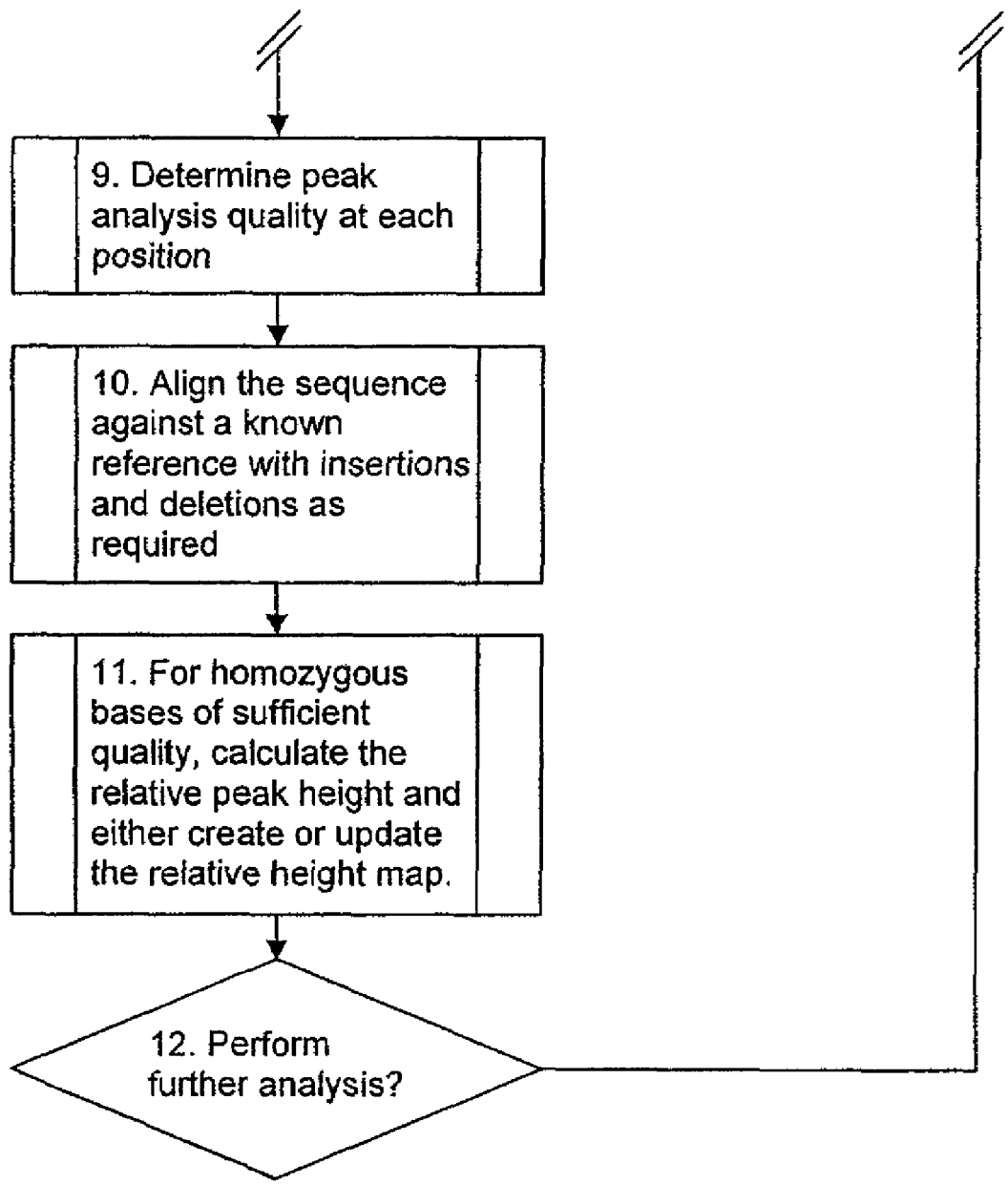
Figure 3A:
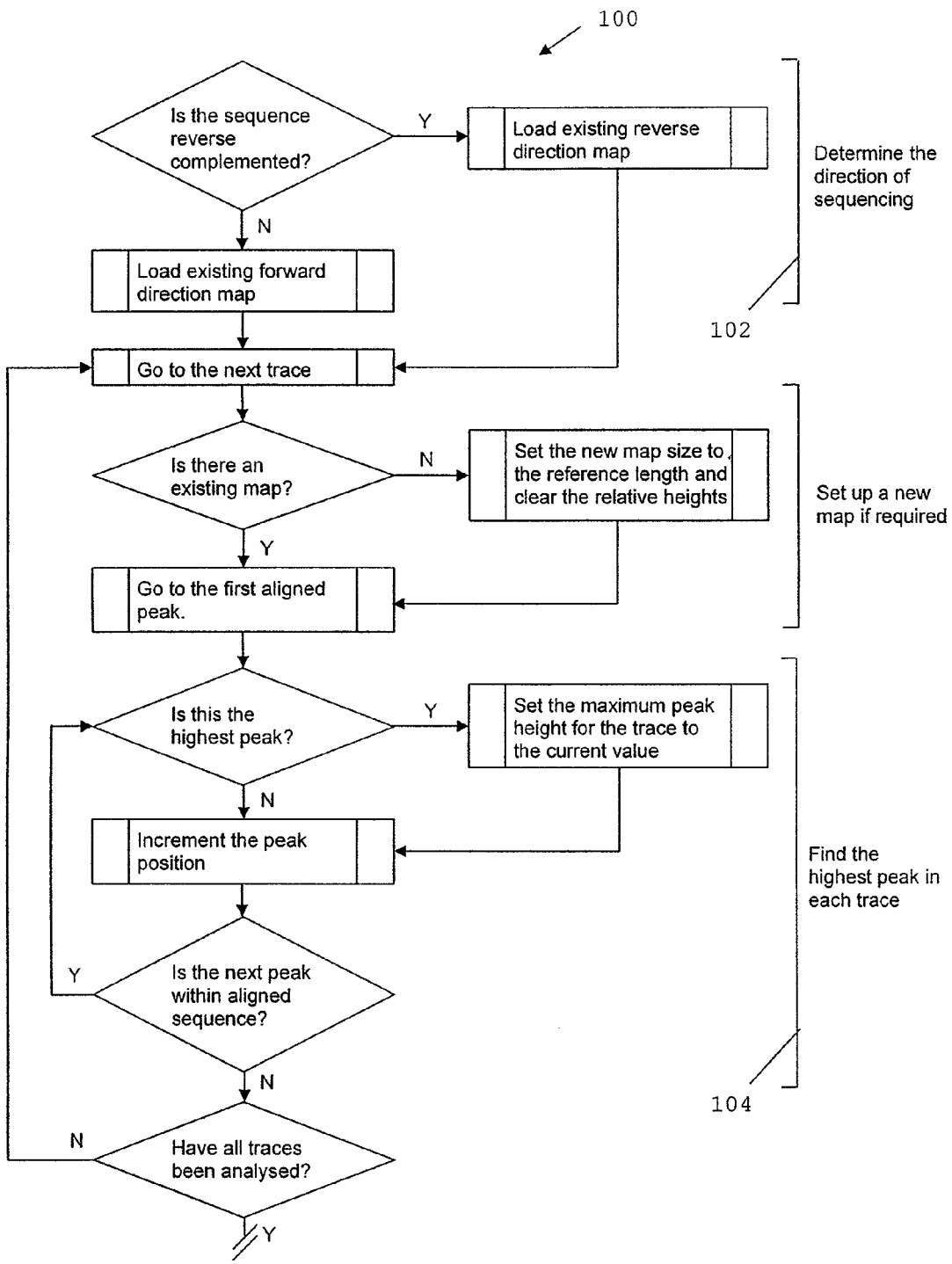
FIGS. 3A-3D illustrate a flow chart showing more detail of the step 12 in FIG. 2B.
Figure 3B:
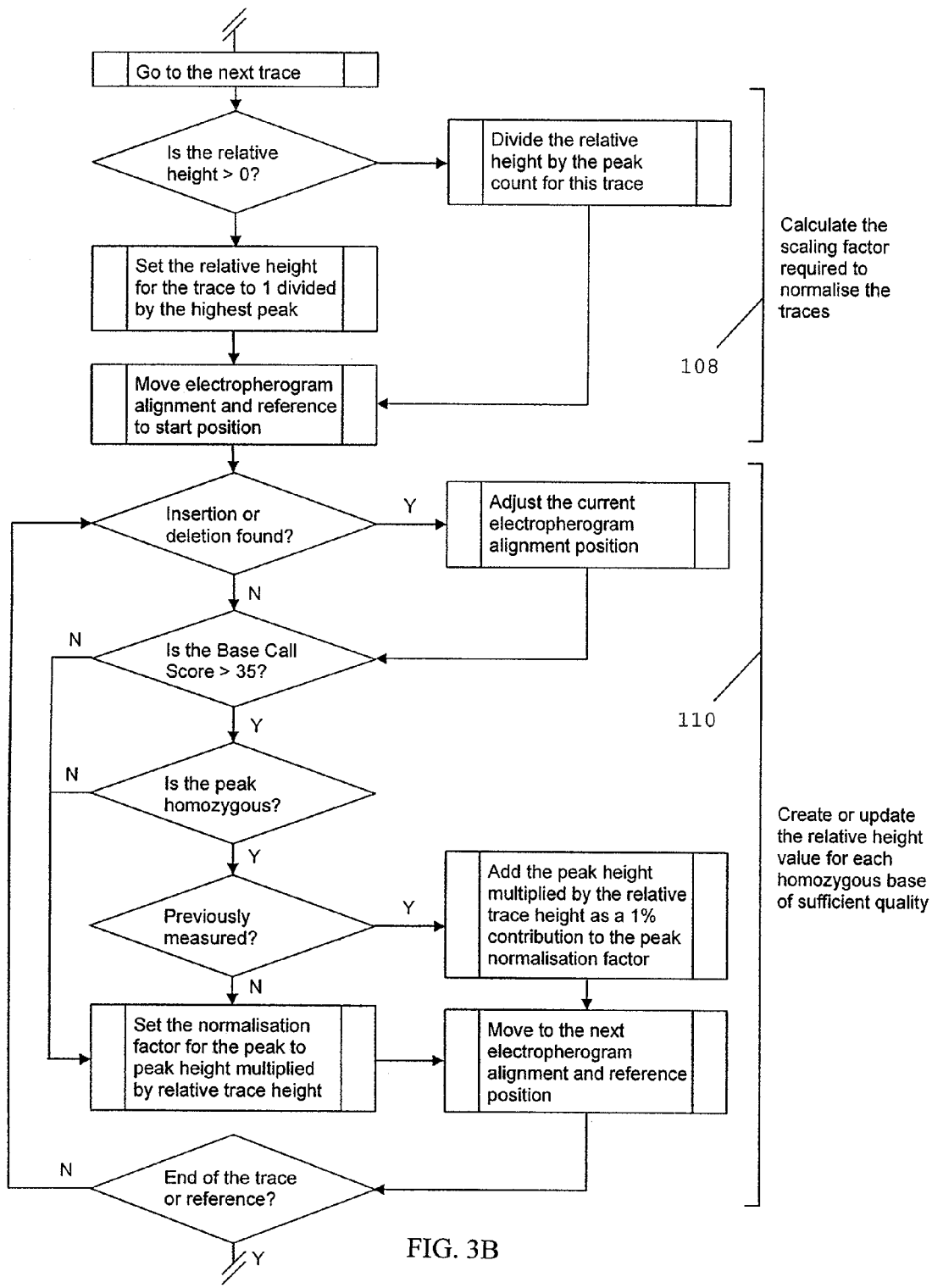
Figure 3C:
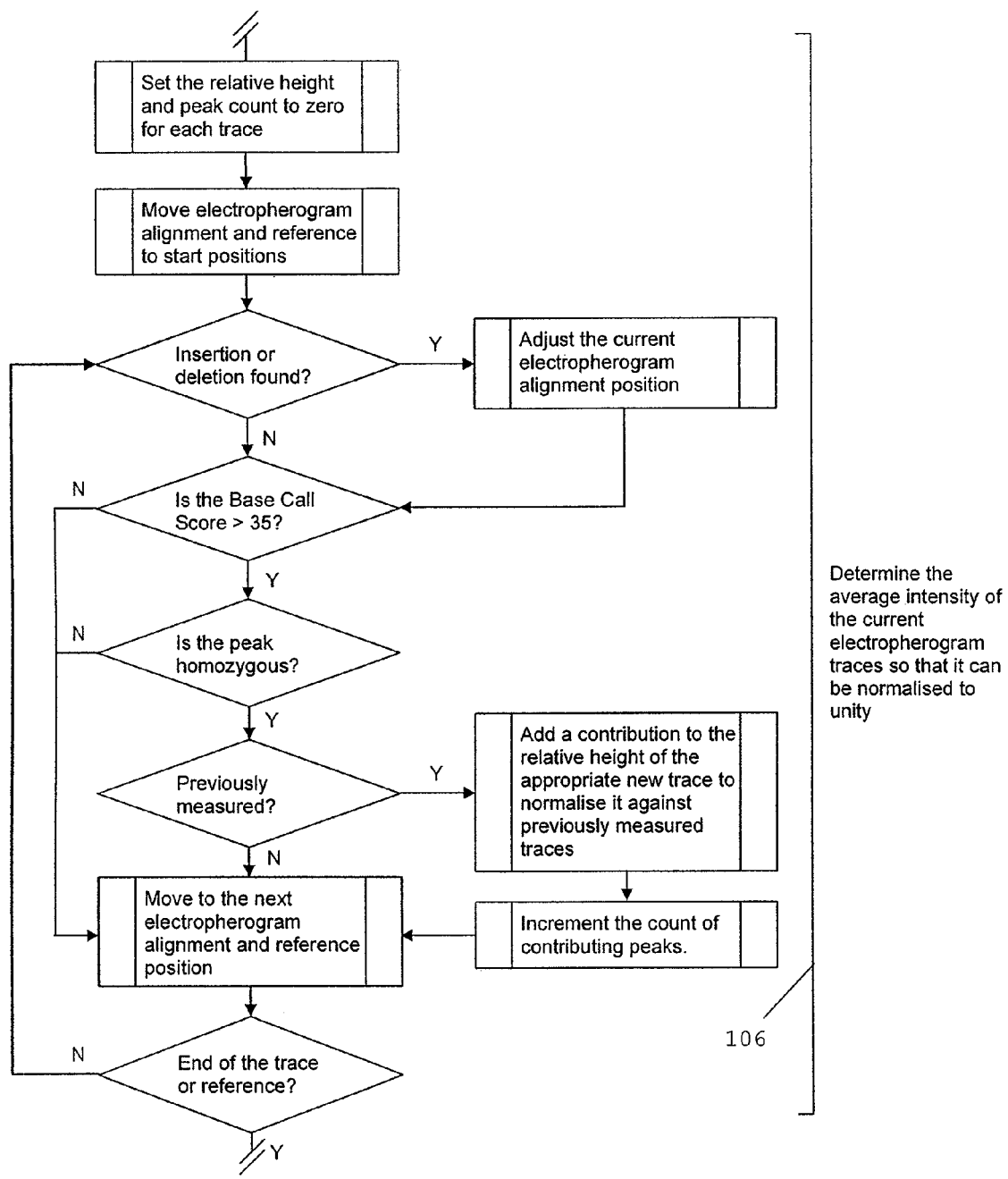
Figure 3D:
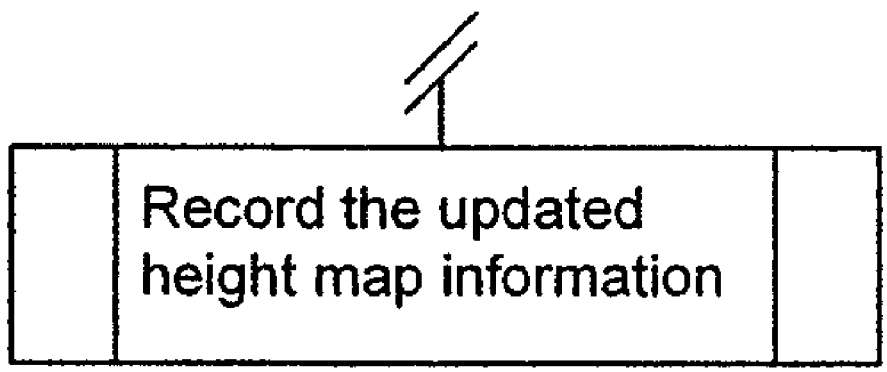

The method of the present invention is described with reference to FIGS. 2 to 4. FIG. 2 shows the process of creating and refining a relative height map according to a preferred embodiment of the present invention. The process commences at 1, where DNA is extracted from a sample of tissue to be analyzed using standard techniques, of Sanger as described above.

At 2, the DNA is amplified using standard techniques, as described above. The required locus is selected by using appropriate primers.

At 3, a sequencing reaction is conducted on the amplified DNA. This will result in a mixture of DNA fragments of varying length. If dye labeled chain terminators are used The composition of the mixture will depend on the relative rates of incorporation of the chain terminating dye labeled nucleotides bases versus the chain extending unlabelled nucleotide bases at each position in the chain. It has been found that this composition does not vary greatly with reaction conditions.

At 4, separation of labeled fragments is performed. The labeled fragments are separated in an electrophoretic DNA analyzer.

At 5, the signals from the fragments are measured. The signal from each of the four nucleotide base types is measured separately, by for example, by using a laser to excite the dye labeled bases. The resultant fluorescence at four distinct frequencies is detected. The strength of the fluorescence is proportional to the concentration of the fragments in the sequencing reaction mixture for each trace. The signal strength measured for each nucleotide type at each base position forms the four trace data sets.

At 6, a spacing analysis is performed to determine peak positions for fragments as fragment size varies. The rate at which a fragment moves through a gel or capillary may be affected by the way in which the DNA chain folds and will vary with chain size. The spacing between peaks is therefore non-uniform and a correction is usually applied to a trace by using a standard mobility shift that is derived by performing an analysis of DNA with a known sequence. Once this function has been completed a spacing analysis can be undertaken by using a software package such as ABI Sequencing Analysis 5.0.

At 7, a fitting procedure is performed to determine peak characteristics. In order to increase the accuracy of the peak height measurements it is beneficial to perform a least squares fitting procedure on each peak. The National Institute of Standards and Technology provides a template for creation of a Levenberg-Marquardt least squares fitting routine. This can be used to fit the peaks to a suitable line shape, e.g. Gaussian or Lorentzian. This will produce a calculated height and width for each peak. The fitting routing is available at the URL: http://nyl.nist.gov/pub/nistpubs/jres/103/6/j36sha.pdf.

At 8, an analysis is performed to determine the bases at each sequence position. The analysis can be performed by a number of commercially available software packages. Sequencing Analysis 5.0 and the PHRED packages are capable of determining a sequence containing mixture of 2 or more bases from an electropherogram signal. Assign SBTTM is capable of performing base calling on sequence mixtures. Details of PHRED can be found at the URL: http://bozeman-.mbt.washington.edu/phrap.docs/phred.html.

At 9, a peak analysis quality at each position is performed. Peak quality can be determined using commercially available packages. Assign contains a peak quality scoring system. PHRED is also capable of generating quality scores. Quality scoring using PHRED is described in Brent Ewing, LaDeana Hillier, Michael C. Wendl, and Phil Green. Base-calling of automated sequencer traces using phred. I. Accuracy assessment. 1998. Genome Research 8:175-185 and Brent Ewing and Phil Green. Base-calling of automated sequencer traces using phred. II. Error probabilities. 1998. Genome Research 8:186-194.

At 10, the sequence is aligned against a known reference to include insertions and deletions as required in order to maximize sequence alignment.

At 11, bases that are not homozygous and of sufficient quality are disregarded. Those that are homozygous and of sufficient quality are used to calculate a relative peak height map. If the base is unfilled in the map the height of the trace become the base height in the map. If the base is already in the map then the current base updates the base height in the map.

The relative height map should be generated from a panel of sequences that include homozygous positions at as many of the possible bases at each position as possible. Bases that have no adjustment should be marked on the output of the software. Subsequent sequences should be used to update the relative height map where the quality of the peaks is sufficient.

At 12, a check is performed of whether further samples are to be included in the generation of the relative height map. If so, the then process returns to step 1, otherwise the map is ready. As further samples become available the relative height map may, and should, be updated.

The process of steps 10 and 11 are described in more detail with reference to FIG. 3. The process shown in FIG. 3 starts generally at 100, where the direction of sequencing is determined at 102. If a map does not already exist a new map is generated at 103, otherwise we go to the first aligned peak in the traces.

At 104, the highest peak in each trace is found. At 106, the average intensity of the current electropherogram traces is determined from homozygous bases with a sufficiently high quality score so that it can be normalized to unity. At 108, the scaling factor required to normalize the traces is calculated. At 110, the relative height value for each homozygous base of sufficient quality is created or updated. From these calculations the relative height of each base within each trace is determined, as well as the relative height of the traces to each other and the scaling factor for each base is the amount of scaling of each peak of each trace needs to be adjusted to be unity for homozygous bases. If a base is not homozygous and is scaled by the scaling factor it will be smaller than unity, in proportion to the fraction of the total sequences containing the base at that position.

This process is described in yet further detail of this embodiment in the pseudo code set forth in the Computer Program Listing Appendix entitled "PSEUDO CODE OF CREATION/UPDATE OF RELATIVE HEIGHT MAP," which is incorporated by reference herein in its entirety.

In order to achieve peak height balancing for a given sequence, at least one homozygous base sequence must be measured to create a peak height map. A homozygous sequence representing the possible mutations or the complete wild type or complete mutant at each polymorphic position is required to achieve a complete analysis of subsequent sequences Peak height maps can be transferred to different sequencers to measure the same genes if the same sequencing chemistry including sequencing polymerase is used.

The relative height map can be loaded as a default on a computer system (such as 200) which has previously not used the present invention; or an existing reference panel on the computer system can be updated. Loading or updating occurs by storing the reference panel in memory 210 or hard disk storage 217 of the computer system. The reference panel is transferred from a portable storage medium (e.g. CD floppy disk, flash memory stick) or by computer network communication.

Once a peak height reference map has been created, the sequence for each new sample can be adjusted to reflect the expected incorporation rate at each position. This will produce an electropherogram trace with even peak heights at homozygous positions. Positions with mixtures of bases will have peaks whose height is proportional to the relative abundance of each constituent in the mixture.

Figure 4A:
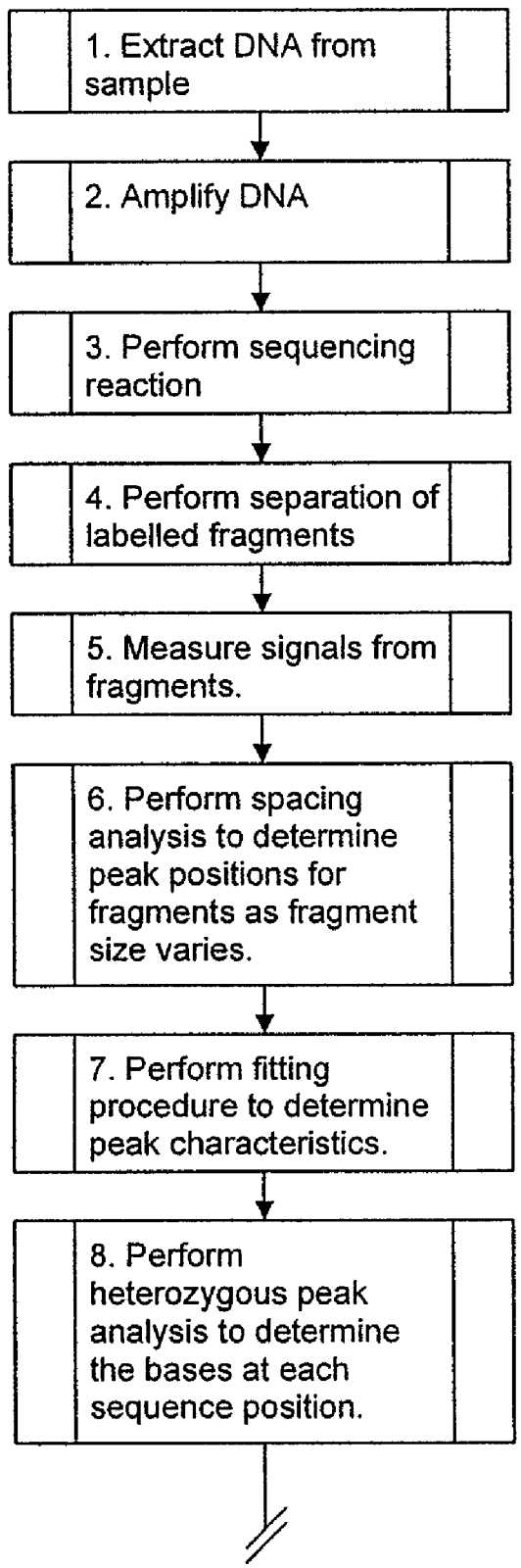
FIGS. 4A-4B illustrate a flow chart showing a second preferred form of the present invention.
Figure 4B:
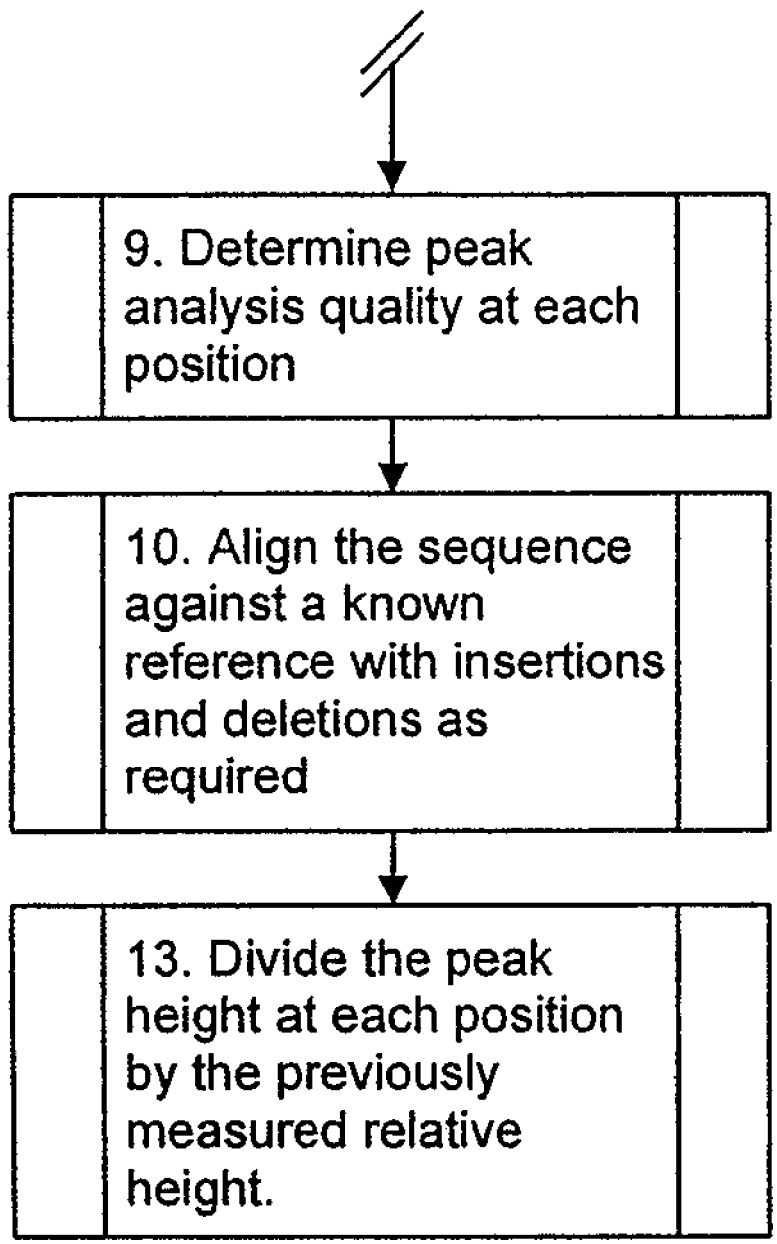

The process of applying the relative peak height map is described in relation to FIG. 4.

Steps 1 to 10 are the same as those of 1 to 10 in FIG. 2. (There is no step 12 in FIG. 4).

At 13, the peak height at each position is divided by the height in the corresponding base position in the peak height map which functions as a scaling factor to produce a normalized trace for the current sample.

Once the signal at each peak has been divided by the previously acquired scaling factor, all homozygous positions will have peak heights of the same approximate size. Positions where there are mixtures of bases will have peaks whose heights reflect the relative proportions of the sequence containing each alternative base. Typically this will be able half the height of the other peaks.

It is possible, to divide each height in the peak height map by the peak height at each new corresponding position of the same, which also functions as a scaling factor. However the ratio is reverse, thus peaks associated with mixtures of bases will be higher than the relative heights of homozygous peaks, rather lower. This technique may be useful if it is desired to have mixed base peaks stand out.

The process of step 13 is described in more detail with reference to FIG. 5. The process shown in FIG. 5 starts generally at 120 in which the direction of sequencing is determined. The data points that contribute to each peak in the traces are adjusted using the previously calculated relative peak heights at 122 to create the scaled traces of the sample.

This process is described in yet further detail of this embodiment in the pseudo code set forth in the Computer Program Listing Appendix entitled "PSEUDO CODE OF APPLYING RELATIVE HEIGHT MAP," which is incorporated by reference herein in its entirety.

The procedure for applying peak height adjustments is described for the analysis of signals from an electrophoretic DNA analyzer. However, it could be applied to any method where signals from DNA fragments are measured.

Figure 5A:
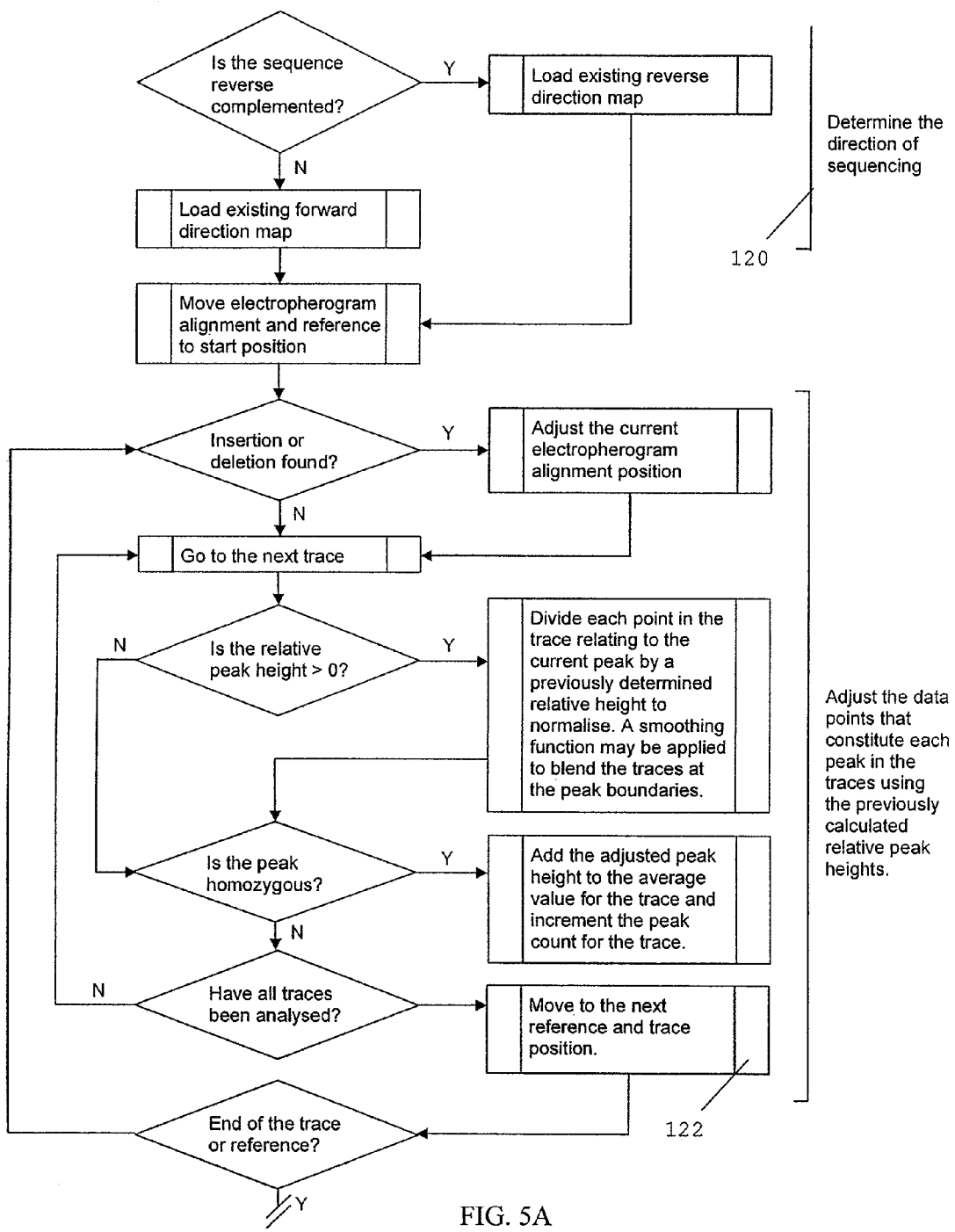
FIGS. 5A-5B illustrate a flow chart showing more detail of the step 13 in FIG. 4B.
Figure 5B:
Figure 6:
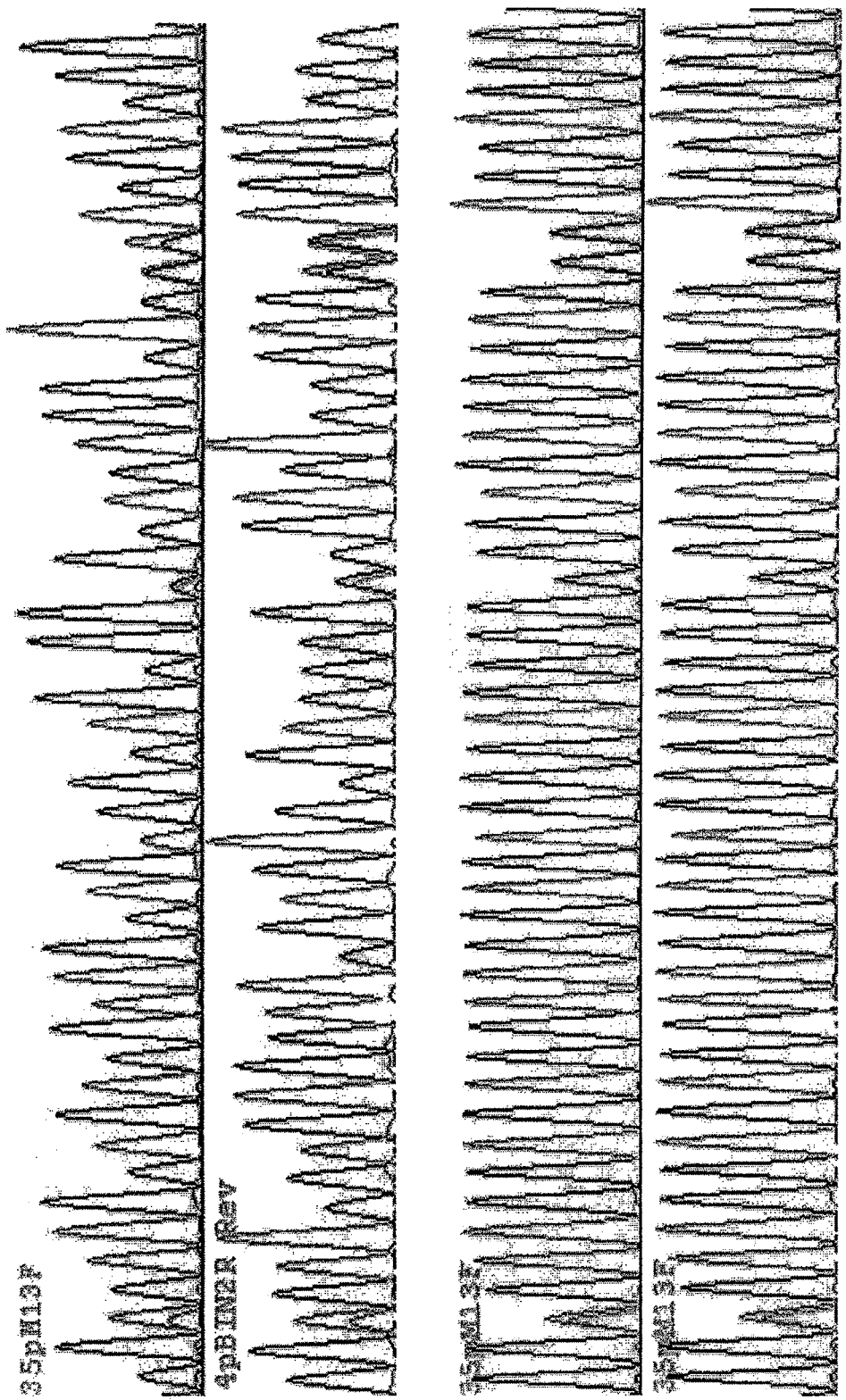
FIG. 6 is a graph showing before and after representation of trace signals of a sample of DNA, the after (on the bottom part) resulting from the application of the aspect of the form of the present invention of FIGS. 4A-4B.

FIG. 6 shows an example of data displayed on a computer display, the computer having used the process of applying scaling to the signal traces using the process described in FIG. 5. The same sequence is shown in the top part and the bottom part.

The top part of the figure shows forward and reverse sequence traces displayed using conventional analysis of the sequence. The bottom part shows forward and reverse sequence traces adjusted using a relative height map obtained from analyzing a panel of 85 sequences from the same locus. The scaling from the adjustment takes into account the relative incorporation rate of CTB to CEB.

The present invention does not directly compare trace results, which occurs in the prior art. The present invention improves base calling, which reduces/eliminates the need for human editing. Variations between sample sequences are determined by comparing the text sequences. The improvement in base calling is performed following the calculation of an expected peak height for every position within a sequence based on an analysis of all traces from tested samples, which is highly reproducible at the same regions within different samples. The scaling process results in a quantitative summary of the data where the peak heights reflect the relative numbers of DNA fragments in the sample.

As a result of improved base calling accuracy nucleotide substitution mutations and mutations resulting in insertions and deletions can also be detected. Furthermore the scaling process results in a quantitative application of DNA sequencing where the peak height relates to the concentration of the appropriate base in the amplified DNA template.

Applications of the present invention include:

1) Genotyping for known nucleotide substitutions (nucleotide substitutions and insertions/deletions). Improved Base calling accuracy simplifies DNA sequencing based genotyping. Sequences on alternative chromosomes may differ between each other as the result of the presence of additional base (s) (insertion) or absence (deletion) of a base(s) relative to the other. When sequenced together at the site of the insertion/deletion the traces representing sequence from each chromosome become out of phase resulting in a series apparently heterozygous positions. Improved base calling of heterozygous sequence enables accurate identification of the sequence. This enables genotyping of heterozygous insertion deletion polymorphisms.

2) Mutation detection (variant detection—nucleotide substitutions and insertions/deletions). Improved base calling accuracy improves the ability to detect unknown sequence variants. This includes the ability to detect and annotate insertion/deletion (indel)polymorphisms by comparing the base calling of the sequence mixtures containing the indel with a reference sequence and determining which sequence bases need to be inserted or deleted in order for the reference sequence and the sample sequence to be aligned. The bases that need to be inserted represent the inserted or deleted sequences in the sample.

3) Mutation quantitation. Normalizing the peak heights results enables the comparison of the quantity of a base at a particular position between different samples or DNA pools. An application may include comparing an HIV sequence from an infected individual to determine if the relative amounts of a mutation have increased or decreased over a period of time. Another application maybe to compare the frequency of a mutation between pools between different populations.

4) Chromosome sequence determination (Haplotyping). Conventional simultaneous sequencing of DNA from both chromosomes may identify differences that exist between the different chromosomes. However it is not possible to determine if two or more sequence differences are on the same or alternate chromosomes. Under certain experimental conditions it is possible to create more DNA fragments from one chromosome than the other. In such a case it is possible to determine the precise sequence that is present on both chromosomes because the sequence peaks from one chromosome will be greater that the peak heights from the alternate chromosome.

Modifications to the present invention may be made, such as:
- the method may be performed on nucleic acids other than DNA;
- DNA may not need to be extracted, i.e. the PCR is performed directly on a sample of tissue without the need for DNA extraction;
- the DNA need not be amplified;
- other applications of the present invention will be readily identified by persons skilled in the art, application of the present invention will therefore not be limited to the used described herein.

Having thus described several aspects of at least one embodiment of this invention, it is to be appreciated various alterations, modifications, and improvements will readily occur to those skilled in the art. Such alterations, modifications, and improvements are intended to be part of this disclosure, and are intended to be within the spirit and scope of the invention. Accordingly, the foregoing description and drawings are by way of example only.

What is claimed is:

1. A method for analyzing nucleic acid sequence data produced by an automated sequencer, said data comprising a trace for each base type, said method comprising
    scaling the data, for each base in each trace by an expected height of the base in a map of relative heights of homozygous base data, with a suitably configured processor of a computer system; and processing the scaled data to produce analyzed results.

2. A method according to claim 1, wherein the method further comprises producing the map of relative heights of homozygous base data.

3. A method according to claim 2, wherein the map is produced by determining an average intensity of the heights of each base position that is homozygous in a trace of each nucleotide type in the sequence data.

4. A method according to claim 3, wherein the map is produced by normalizing the sequence data relative to the average intensity.

5. A method according to claim 3, wherein the average intensity for each trace is determined by scaling the height of each base position that is homozygous relative to the highest of the heights of each base position for each trace.

6. A method according to claim 5, wherein the map is adjusted by a contribution of the height to each base position that is homozygous for each trace from sequence data of subsequent different samples.

7. A method according to claim 6, wherein each contribution is smaller than the existing relative height at each corresponding position in the relative height map.

8. A method according to claim 2, wherein the sequence data comprises a trace for each nucleotide type, with each trace defined by a series of peaks at base positions in which a nucleotide base of the type corresponding to the trace type is present, wherein the map is produced by finding a scaling factor at each base position in the map that normalizes the peak height of homozygous bases.

9. A method according to claim 8, wherein the scaling factor for each base position is determined by taking the highest peak in each trace and dividing it by the height of the peak at that base position for each base position in each trace.

10. A method according to claim 8, wherein an average intensity of each trace is calculated.

11. A method according to claim 10, wherein the scaling factor for each base position is calculated by dividing average intensity of the respective trace by the peak height at that base position.

12. A method according to claim 10, wherein the average intensity is calculated by accumulating a measure of the relative height of each peak that has a non-zero contribution and then dividing this by the number of peaks contributing to the accumulation.

13. A method according to claim 8, wherein the scaling factor is adjusted by comparing each base peak height in a subsequent different sample to each previous peak height and normalizing the average intensity to unity.

14. A method according to claim 8, wherein the relative height for each base is updated by multiplying the height of the sequence data at each base position for each nucleotide type by a corresponding scaling factor of the map.

15. A method according to claim 8, wherein an updated relative peak height is determined by adding a small percentage of the peak height of each base multiplied by the scaling factor to the current relative peak height.

16. A method according to claim 1, wherein a different sample is added to the relative height map by aligning a base position in the different sample with the same bases in the relative height map.

17. A method of producing a normalized set of electropherogram trace signals of a nucleic acid sequence of a sample comprising:
    providing first electropherogram signal data from a first sequence obtained using a given nucleic acid sequencing chemistry, the signal data comprising a trace of the detection signal for each type of base at each base position in the nucleic acid sequence;
    creating a relative height map of the intensities of each trace at each base position from the first electropherogram signal data;
    obtaining second electropherogram signal data of a different sample using the same nucleic acid sequencing chemistry;
    scaling, using a computer, the second electropherogram signal data for each base in each trace by the expected height of the base in the relative height map to produce a normalized base data set; and
    storing, in a memory of the computer, the normalized base data set for subsequent analysis.

18. A method of detecting mixtures of bases in a nucleic acid sequence comprising:
    determining whether each base in the stored normalized base data set produced using the method of claim 17 has a significantly lower height than the expected height and in the event that it does registering the base as a mixture.

19. A method of indicating mixtures of bases in a nucleic acid sequence comprising:
    displaying the normalized base data set produced using the method of claim 17, with mixtures of bases being indicated as having a significantly lower height than the expected height of a homozygous base.

20. A method of sequencing DNA comprising:
    providing a sample of tissue;
    extracting DNA from the sample of tissue;
    amplifying the extracted DNA;
    conducting a sequencing reaction on the amplified DNA to produce a mixture of DNA fragments labeled with a nucleotide type indicator;
    separating the labeled fragments in an electrophoretic DNA analyzer;

measuring the signals from the separated fragments to determine a sequence;

performing a spacing analysis to determine peak positions for fragments as fragment size varies;

performing a fitting procedure to determine peak characteristics;

scaling each peak according to a relative height map of the expected peak heights of each trace at each base position determined from reference data obtained using the same chemistry in the sequencing reaction; and storing, in a memory of a computer system, the scaled peaks as a representation of the sequenced DNA.

21. A method of analyzing a nucleic acid sequence comprising:

mapping a relative signal strength of bases of the nucleic acid sequence to form a relative height map;

comparing, using a computer, a sample to the map to determine whether a signal strength of a sample is close to the signal strength of the map for each nucleotide type at each base position, so that when the signal strength of the sample is close to the signal strength of one of a plurality of nucleotide types in the map, then the nucleotide at that base position is considered to be that nucleotide type and is homozygous, and when the sample signal strength is significant for a plurality of nucleotide types at that base then for those nucleotide types which have a significant signal strength are regarded as being present and that base is a mixed base; and storing, in a memory of the computer, the results of the comparison.

22. A method of mapping the relative signal strength of bases to form a relative height map comprising the steps of:

a) obtaining a trace signal for each nucleotide type over a plurality of base positions from a plurality of samples of DNA;

b) discarding the signal at base positions that are not of sufficiently high quality;

c) discarding the signal at base positions that are not homozygous;

d) mapping, using a computer, the height of the trace signal for each trace for each base position by determining an average intensity of non-discarded heights of each base position of each trace from the plurality of samples;

e) repeating steps (a), (b), (c) and (d) until the height at all of the bases desired to be mapped are mapped; and f) storing, in a memory of the computer, the mapped trace signals for use in analyzing another DNA sample.

23. A nucleic acid sequencing apparatus configured to perform a method for analyzing nucleic acid sequence data produced by an automated sequencer, the data comprising a trace for each base type, the apparatus comprising means for scaling the data for each base in each trace by an expected height of the base in a map of relative heights of homozygous base data; and means for processing the scaled data to produce analyzed results.

24. A computer readable storage medium encoded with a computer program for execution on a processor, the program when executed on the processor performing a method of analyzing nucleic acid sequence data produced by an automated sequencer, the data comprising a trace for each base type, the method comprising, scaling the data for each base in each trace by an expected height of the base in a map of relative heights of homozygous base data; and processing the scaled data to produce analyzed results.

25. A computer readable storage medium encoded with a computer program for execution on a processor, the program when executed on the processor performing a method of producing a normalized set of electropherogram trace signals of a nucleic acid sequence of a sample comprising instructions which when executed control a data processing device to:

provide first electropherogram signal data from a first sequence obtained using a given nucleic acid sequencing chemistry, the signal data comprising a trace of the detection signal for each type of base at each base position in the nucleic acid sequence;

create a relative height map of the intensities of each trace at each base position from the first electropherogram signal data;

obtain second electropherogram signal data of a different sample using the same nucleic acid sequencing chemistry;

scale the second electropherogram signal data for each base in each trace by the expected height of the base in the relative height map to produce a normalized base data set; and store the normalized base data set for subsequent analysis.

26. A computer readable storage medium encoded with a computer program for execution on a processor, the program when executed on the processor performing a method of controlling a data processing device to conduct a method of sequencing DNA comprising instructions which when executed control a data processing device to:

provide a sample of tissue;

extract DNA from the sample of tissue;

amplify the extracted DNA;

conduct a sequencing reaction on the amplified DNA to produce a mixture of DNA fragments labeled with a nucleotide type indicator;

separate the labeled fragments in an electrophoretic DNA analyzer;

measure the signals from the separated fragments to determine a sequence;

perform a spacing analysis to determine peak positions for fragments as fragment size varies;

perform a fitting procedure to determine peak characteristics;

scale each peak according to a relative height map of the expected peak heights of each trace at each base position determined from reference data obtained using the same chemistry in the sequencing reaction; and output the scaled peaks as a representation of the sequenced DNA.

27. A computer readable storage medium encoded with a computer program for execution on a processor, the program when executed on the processor performing a method of analyzing a nucleic acid sequence comprising instructions which when executed control a data processing device to:

map the relative signal strength of bases to form a relative height map;

compare a sample to the map to determine whether a signal strength of a sample is close to the signal strength of the map for each nucleotide type, at each base position, so that when the signal strength of the sample is close to the signal strength of one of a plurality of nucleotide types in the map, then the nucleotide at that base position is considered to be that nucleotide type and is homozygous, and when the signal strength significant for a plurality of nucleotide types at that base position then for those nucleotide types which have a significant signal strength are recorded as being present and that base is a mixed base; and output the results of the comparison.

28. A computer readable storage medium encoded with a computer program for execution on a processor, the program when executed on the processor performing a method of mapping the relative signal strength of bases to form a relative height map comprising instructions which when executed control a data processing device to:
   a) obtain a trace signal for each nucleotide type over a plurality of base positions from a plurality of samples of DNA;
   b) discard the signal at base positions that are not of sufficiently high quality;
   c) discard the signal at base positions that are not homozygous;
   d) map the height of the trace signal for each trace for each base position by determining an average intensity of non-discarded heights of each base position of each trace from the plurality of samples;
   e) repeat steps (a), (b), (c) and (d) until the height at all of the bases desired to be mapped are mapped; and
   f) store the mapped trace signals for use in analyzing a DNA sample.

29. An apparatus for analyzing nucleic acid sequence data produced by an automated sequencer, the data comprising a trace for each base type, the apparatus comprising a processor means for scaling the data for each base in each trace by an expected height of the base in a map of relative heights of homozygous base data, wherein the processor is configured to process the scaled data to produce analyzed results.

30. An apparatus for producing a normalized set of electropherogram trace signals of a nucleic acid sequence of a sample comprising:
   means for providing first electropherogram signal data from a first sequence obtained using a given nucleic acid sequencing chemistry, the signal data comprising a trace of the detection signal for each type of base at each base position in the nucleic acid sequence;
   means for creating a relative height map of the intensities of each trace at each base position from the signal data;
   means for creating a relative height map of the intensities of each trace at each base position from the first electropherogram signal data;
   means for obtaining second electropherogram signal data of another sample using the same nucleic acid sequencing chemistry;
   means for scaling the second electropherogram signal data for each base in each trace by the expected height of the base in the relative height map to produce a normalized base data set; and
   means for storing the normalized base data set for subsequent analysis.

31. An apparatus for detecting a mixture of bases in a nucleic acid sequence comprising:
   means for determining whether each base in the normalized base data set produced using the apparatus of claim 30 has a significantly lower height than the expected height and in the event that it does register the base as a mixture.

32. An apparatus for indicating a mixture of bases in a nucleic acid sequence comprising:
   means for displaying the scaled data set produced using the apparatus of claim 30, with mixtures of bases being indicated as having a significantly lower height than the expected height of a homozygous base.

33. An apparatus for sequencing DNA comprising:
   means for receiving a sample of tissue;
   means for extracting DNA from the sample of tissue;
   means for amplifying the extracted DNA;
   means for conducting a sequencing reaction on the amplified DNA to produce a mixture of DNA fragments labeled with a nucleotide type indicator;
   means for separating the labeled fragments;
   means for measuring the signals from the separated fragments to determine a sequence;
   means for performing a spacing analysis to determine peak positions for fragments as fragment size varies;
   means for performing a fitting procedure to determine peak characteristics;
means for scaling each peak according to a relative height map of the expected heights of each trace at each base position determined from reference data obtained using the same chemistry in the sequencing reaction; and
   means for outputting the scaled peaks as a representation of the sequenced DNA.

34. An apparatus for analyzing a nucleic acid sequence comprising:
   means for mapping a relative signal strength of bases of the nucleic acid sequence to form a relative height map;
   means for comparing a sample to the map to determine whether a signal strength of a sample is close to the signal strength of the map for each nucleotide type at each base position, so that when the sample signal strength is close to the signal strength of one of a plurality of nucleotide types, then the nucleotide at that base is considered to be that nucleotide type and is homozygous, and when the sample signal strength is significant for a plurality of nucleotide types of that base, then those nucleotide types which have a significant signal strength are regarded as being present and that base is a mixed base; and
   means for outputting the results of the comparison.

35. An apparatus for mapping the relative signal strength of bases to form a relative height map comprising:
   a) means for obtaining a trace signal for each nucleotide type over a plurality of base positions from a plurality of samples of DNA;
   b) means for discarding the signal at base positions that are not of sufficiently high quality;
   c) means for discarding the signal at base positions that are not homozygous;
   d) means for mapping the height of the trace signal for each trace for each base position by determining an average intensity of non-discarded heights of each base position of each trace from the plurality of samples;
   wherein the means of (a), (b), (c) and (d) are used again until the height at all of the bases desired to be mapped are mapped; and
   e) means for storing the mapped trace signals for use in analyzing another DNA sample.

36. A method according to claim 1, further comprising interpreting the scaled data to identify the bases present and producing a text sequence.

37. A method according to claim 1, wherein the processing comprises quantitating a proportion of nucleic acid bases in the sequence data.

38. A method according to claim 1, wherein the processing comprises base calling.

39. A method according to claim 1, wherein the suitably configured processor is configured to operate as a nucleic acid sequence data analyzer.

40. A method according to claim 1, further comprising outputting the analyzer results for storage or use by a person or a machine.

* * * * *